(12) United States Patent
Lehmann (10) Patent No.: US 10,603,253 B2
(45) Date of Patent: Mar. 31, 2020

(54) SKIN CARE FABRIC (71) Applicant: FILAG Medical Schweiz AG, Schaffhausen (CH)

(72) Inventor: Markus Lehmann, Zürich (CH)

(73) Assignee: Filag Medical Schweiz AG, Schaffhausen (CH)

( * ) Notice: Subject to any disclaimer, the term of this patent is extended or adjusted under 35 U.S.C. 154(b) by 0 days.

(21) Appl. No.: 16/239,053

(22) Filed: Jan. 3, 2019

(65) Prior Publication Data
US 2019/0231653 A1 Aug. 1, 2019

Related U.S. Application Data (60) Provisional application No. 62/625,247, filed on Feb. 1, 2018.

(51) Int. Cl.
| | | |
|---|---|---|
| *A61K 8/02* | (2006.01) | |
| *D06C 21/00* | (2006.01) | |
| *D04B 21/04* | (2006.01) | |
| *A45D 34/04* | (2006.01) | |
| *D06C 13/08* | (2006.01) | |
| *A61Q 19/00* | (2006.01) | |
| *A61K 9/70* | (2006.01) | |
| *A61K 9/127* | (2006.01) | |
| *A61K 8/11* | (2006.01) | |
| *D06C 11/00* | (2006.01) | |
| *D04B 21/16* | (2006.01) | |
| *D06M 11/38* | (2006.01) | |
| *D06M 23/12* | (2006.01) | |
| *D06M 11/84* | (2006.01) | |
| *A47K 7/03* | (2006.01) | |
| *D06M 101/32* | (2006.01) | |
| *D06M 101/34* | (2006.01) | |

(52) U.S. Cl.
CPC ............ *A61K 8/0208* (2013.01); *A45D 34/04* (2013.01); *A61K 8/11* (2013.01); *A61K 9/127* (2013.01); *A61K 9/7007* (2013.01); *A61Q 19/00* (2013.01); *D04B 21/04* (2013.01); *D04B 21/16* (2013.01); *D06C 11/00* (2013.01); *D06C 13/08* (2013.01); *D06C 21/00* (2013.01); *D06M 11/38* (2013.01); *D06M 11/84* (2013.01); *D06M 23/12* (2013.01); *A45D 2200/1036* (2013.01); *A47K 7/03* (2013.01); *A61K 2800/28* (2013.01); *D06M 2101/32* (2013.01); *D06M 2101/34* (2013.01); *D10B 2331/02* (2013.01); *D10B 2331/04* (2013.01); *D10B 2403/0111* (2013.01); *D10B 2509/00* (2013.01)

(58) Field of Classification Search
CPC .... A61K 8/0208; A61K 9/7007; A61K 9/127; A61K 8/11; A61K 2800/28; A45D 34/04; A45D 2200/1036; A47K 7/03; A61Q 19/00; D06C 21/00; D06C 13/08; D06C 11/00; D04B 21/04; D04B 21/16; D06M 11/38; D06M 23/12; D06M 11/84; D06M 2101/32; D06M 2101/34; D10B 2403/0111; D10B 2509/00; D10B 2331/02; D10B 2331/04
See application file for complete search history.

(56) References Cited

U.S. PATENT DOCUMENTS

| | | | | |
|---|---|---|---|---|
| 2003/0228351 | A1* | 12/2003 | Hasenoehrl | A47K 7/03 424/443 |
| 2010/0322989 | A1* | 12/2010 | Martin | A61K 8/0208 424/402 |
| 2013/0189473 | A1* | 7/2013 | Sun | D06C 11/00 428/91 |
| 2019/0008623 | A1* | 1/2019 | Nemoto | D04B 21/16 |

FOREIGN PATENT DOCUMENTS

| | | | | |
|---|---|---|---|---|
| DE | 202010014723 | * | 11/2011 | ............ C11D 17/04 |
| JP | 2005245739 | | 9/2005 | |

OTHER PUBLICATIONS

DE202010014723 Machine Translation (Year: 2010).*

* cited by examiner

*Primary Examiner* — Sean M Basquill
(74) *Attorney, Agent, or Firm* — Dority & Manning, P.A.

(57) ABSTRACT

A skin care fabric for medical, pharmaceutical or cosmetic use includes at least 80% by weight of microfibers that are a mixture of polyamide and polyester and have a diameter of less than 50 microns. Each microfiber is split to produce fine fibers closely packed in a parallel structure having a capillary effect and an abrasive effect. The fabric has a surface weight of less than 180 g/m² and is loaded with medical, pharmaceutical or cosmetic active agents. The skin care fabric includes a warp-knitted fabric having a first surface and a second surface opposite the first surface, which is mechanically roughened and cut to become fluffy and yet short-haired and compact and resulting in a further surface enlargement of the fabric structure and a water absorbency of at least four times the surface weight of the fabric.

18 Claims, 6 Drawing Sheets

1 mm  magnification: 41 x

Fig. 3

1 mm  magnification: 41 x

Fig. 4

1 mm  magnification: 41 x  Fig. 5

1 mm  magnification: 41 x  Fig. 6

10 μm    magnification: 1500 x    Fig. 7

10 μm    magnification: 1500 x    Fig. 8

100 μm    magnification: 100 x                Fig. 9

200 μm    magnification: 75 x                 Fig. 10

200 μm    magnification: 150 x    Fig. 11

20 μm    magnification: 680 x    Fig. 12

SKIN CARE FABRIC

CROSS-REFERENCE TO RELATED APPLICATIONS

Not applicable

STATEMENT REGARDING FEDERALLY SPONSORED RESEARCH OR DEVELOPMENT

Not applicable

FIELD OF THE INVENTION

The present invention related to a skin care fabric for medical, pharmaceutical or cosmetic use comprising at least 80% by weight of microfibers whose fibers have a diameter of less than 50 microns and are a mixture of polyimide and polyester, wherein the fabric has been subjected to a splitting process by an alkaline solution treatment, splitting each microfiber producing fine fibers closely packed in a parallel structure having a capillary effect and an abrasive effect, and whereas the fabric is loaded with medical, pharmaceutical or cosmetic active agents.

BACKGROUND

Skin care fabrics are known for various uses, in particular for facial use. They usually come in sheet sizes practical to hold in one hand, and often they are folded in a box for the user to pick one separate sheet. These are generally made of cellulose, which makes them very inexpensive. Unfortunately, because those fabrics tend to rend easily when used in a wet condition, they are not suitable in a moist environment.

The fabric described in US Patent Application Publication No. 2010-0322989, which is hereby incorporated herein by this reference for all purposes, is a skin care tissue with an abrasive effect and consists of microfibers that are loaded with active agents and intended for one-time and wet use. The textile surface has undergone a splitting process. The tissue has a grid structure and grid intermediate spaces or interstices. The effect of this grid was to create space for the split microfiber filaments, which are loaded with the active agents.

During use, the fabric is wetted, normally with water, which washes out the active agents in the fabric and brings them to the skin. According to the active agents, they may then clean the skin, disinfect, apply a cream or moisturizer or provide a pharmaceutical product for medicinal treatment of a region of the skin.

EXEMPLARY OBJECTS AND SUMMARY OF EMBODIMENTS OF THE INVENTION

It is an object of the present invention to provide a skin care fabric for medical, pharmaceutical or cosmetic use but with an improved water absorbance. It has been found that the water absorbency is an important criterion for the usefulness of such a fabric. When for example cleaning one's face, it is important that the fabric is wet enough, but does not drip. Also for medical use, it is important that no drops or splits pollute the surrounding. On the other hand, the fabric itself should not be too heavy, have a firm grip and feels soft on the face. It is further desired that the fabric does not shed loose fibers that are left on the skin of the user.

The skin care fabric according to the invention has a surface weight of less than 180 $g/m^2$ and is a warp-knitted fabric. The skin care fabric according to the invention has a first surface and a second surface, which desirably is formed on a side of the fabric that is opposite the side of the fabric where the first surface is formed. Moreover, the first surface is mechanically roughened and cut, thereby making it fluffy and yet short-haired and compact in order to leave as few fibers as possible on the skin during use and resulting in a further surface enlargement of the fabric structure, having a water absorbency of at least four times the surface weight of the fabric. The second surface is not mechanically roughened. However, the warp-knitted structure on the second surface enables a firm grip in a hand of a user during use of the fabric. The fabric according to the invention is for single-use utilization and can be recycled.

During use, the fabric is wetted, normally with water, which washes out the active agents in the fabric and brings them to the skin. According to the active agents, they may then clean the skin, disinfect it, apply a cream or moisturizer on it and/or provide the skin with a pharmaceutical product. It can be used on normal skin as well as on wounded and scarred skin.

According to one aspect of the invention, the fabric is relatively low in weight by surface area, which is also an economic advantage for a single-use fabric, since the use of raw material is reduced.

It has been found that the structure of the fabric is important for the capability of storing a fluid. For this reason, the fabric according to an embodiment of the invention is a warp knitted fabric. Warp knitting is a family of knitting methods in which the yarn zigzags along the length of the fabric, i.e., following adjacent columns of knitting, rather than a single row. For comparison, knitting across the width of the fabric is called weft knitting.

Since warp knitting requires that the number of separate strands of yarn ("ends") equals the number of stitches in a row, warp knitting is almost always done by machine rather than by hand. All warp-knit fabrics can be stretched and are much more flexible than woven fabrics. After cutting a woven fabric, a warp or weft may get loose which is not desired by a user of a skin fabric. This cannot happen with warp-knit fabrics. Furthermore, and in contrast to normal knitted fabrics, warp-knit fabrics are resistant to runs. Due to the relatively complex making with the many loops, the thickness of a warp-knit fabric is relatively high and the fabric itself is very compact. These structural features facilitate the storage of water inside the fabric and reduces liquid dripping from the fabric. It has therefore been found, that the presently preferred fabric for the use described above is a warp-knit fabric.

The warp-knitted fabric undergoes a splitting process that splits the microfibers into numerous filaments. This process enlarges the surface area of the fabric, and the enlarged surface area enables a greater amount of active agents to be bound on the fabric. Furthermore, the capillary effect further holds the water in the interstices between the fine filament members. The abrasive effect of the fabric results from the relatively sharp edges of the filament, having a three-cornered cross section. Due to the abrasive effect the dry cells on the skin can be removed easily, supported by the large amount of water washing the skin.

The mechanically roughened and cut side of the first surface of the fabric further enlarges the surface area of the fibers. The cutting eliminates short ends and defines a flat surface. Preferably, the roughened and cut side is then compressed and/or sanforized to become more compact and to prevent filament fibers from coming loose and sticking on the skin during use. Furthermore, water absorption is best when the fabric is compact so as to provide a large amount of interstices forming capillary gaps. This first surface nonetheless remains fluffy. Although for some embodiments it is possible to treat the second surface the same as the first surface, it is preferred that the second surface stays in the original state and is not roughened and cut. The second surface is the slightly shinier surface and lends itself to being firmly gripped by the user, whereas the first surface resembles flannel and has a duller appearance and soft to the touch of the user.

In a presently preferred embodiment, the fabric according to the invention comprises a pure polyamide fiber in addition to the microfiber, being much thinner than the microfiber. This has the advantage to hold together the warp-knitted fabric after the splitting process, since the polyamide fiber is not affected by the splitting process.

In a further presently preferred embodiment, the active agents are encapsulated in liposomes. This is an advantage to deliver pharmaceutical agents, drugs. Liposomes are composite structures made of phospholipids and may contain small amounts of other molecules. Though liposomes can vary in size from low micrometer range to tens of micrometers, unilamellar liposomes are typically in the lower size range in order to allow for their surface-attachment and accumulation in pathological areas for treatment of disease.

Further presently preferred embodiments are described below.

BRIEF DESCRIPTION OFF THE DRAWINGS

The accompanying drawings, which are incorporated in and constitute a part of this specification, illustrate at least one presently preferred embodiment of the invention as well as some alternative embodiments. The figures in these drawings, together with the written description, serve to explain the principles of the invention but by no means are intended to be exhaustive of all of the possible manifestations of the invention. Aspects and advantages of the invention are set forth in the description herein, or may be obvious from the description, or may be learned through practice of embodiments of the invention. Those of ordinary skill in the art will better appreciate the features and aspects of such embodiments, and others, upon review of the specification. A full and enabling disclosure of the present invention, including the best mode thereof to one skilled in the art, is set forth more particularly in this specification, including reference to the accompanying figures, in which.

DESCRIPTION OF EXEMPLARY EMBODIMENTS OF THE INVENTION

Reference will now be made in detail to present exemplary embodiments of the invention, wherein one or more examples of which are illustrated in the accompanying drawings. The detailed description uses numerical designations to refer to features in the drawings. Like or similar designations in the drawings and description have been used to refer to like or similar parts of the embodiments of the invention.

Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

It is to be understood that the ranges and limits mentioned herein include all sub-ranges located within the prescribed limits, inclusive of the limits themselves unless otherwise stated. For instance, a range from 100 to 200 also includes all possible sub-ranges, examples of which are from 100 to 150, 170 to 190, 153 to 162, 145.3 to 149.6, and 187 to 200. Further, a limit of up to 7 also includes a limit of up to 5, up to 3, and up to 4.5, as well as all sub-ranges within the limit, such as from about 0 to 5, which includes 0 and includes 5 and from 5.2 to 7, which includes 5.2 and includes 7.

Figure 1:
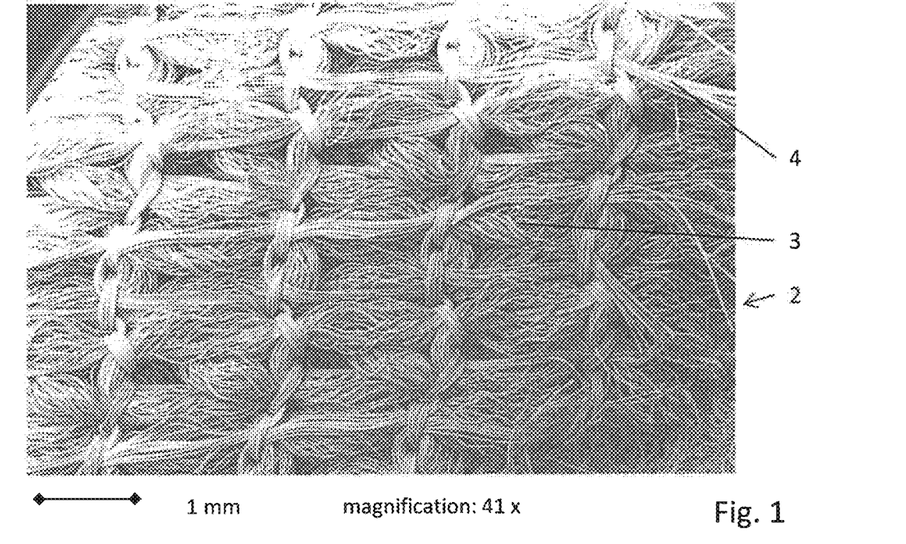
FIG. 1 shows a picture of the second surface of an inventive fabric with a magnification factor 41 times the actual size, but before the microfibers are subjected to splitting.
Figure 2:
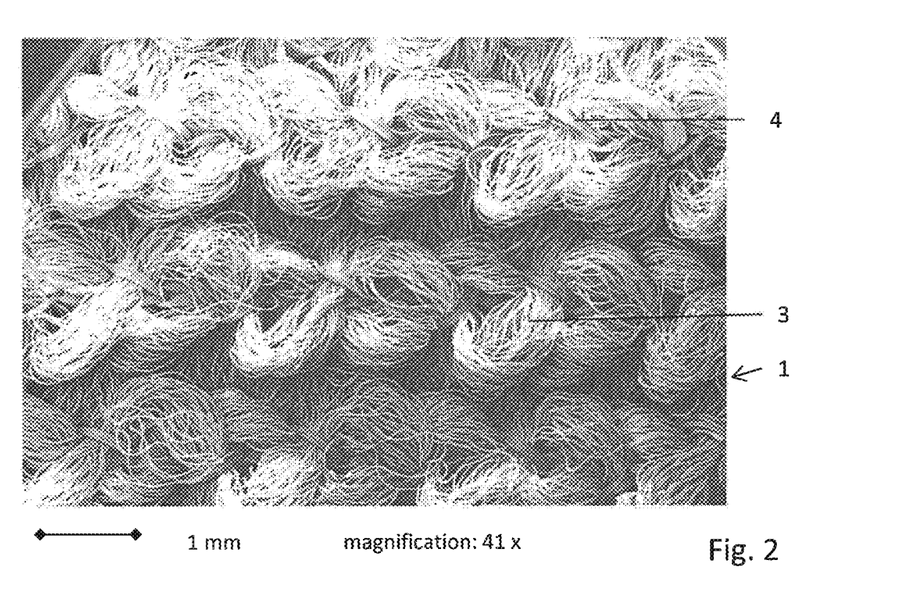
FIG. 2 shows a picture of the first surface of an inventive fabric with a magnification factor 41 times the actual size, but before the microfibers are subjected to splitting.

FIG. 1 shows an embodiment of a second surface 2 of a skin care fabric for medical, pharmaceutical or cosmetic use comprising at least 80% by weight of microfibers 3 whose fibers have a diameter of less than 50 microns and are a mixture of polyamide and polyester. The fabric has a surface weight of less than 180 g/m2, and the fabric is a warp-knitted fabric. FIG. 2 shows an embodiment of a first surface 1 of the embodiment of a skin care fabric shown in FIG. 1. However, in FIGS. 1 and 2, the fabric is shown in its unprocessed and untreated state.

Figure 3:
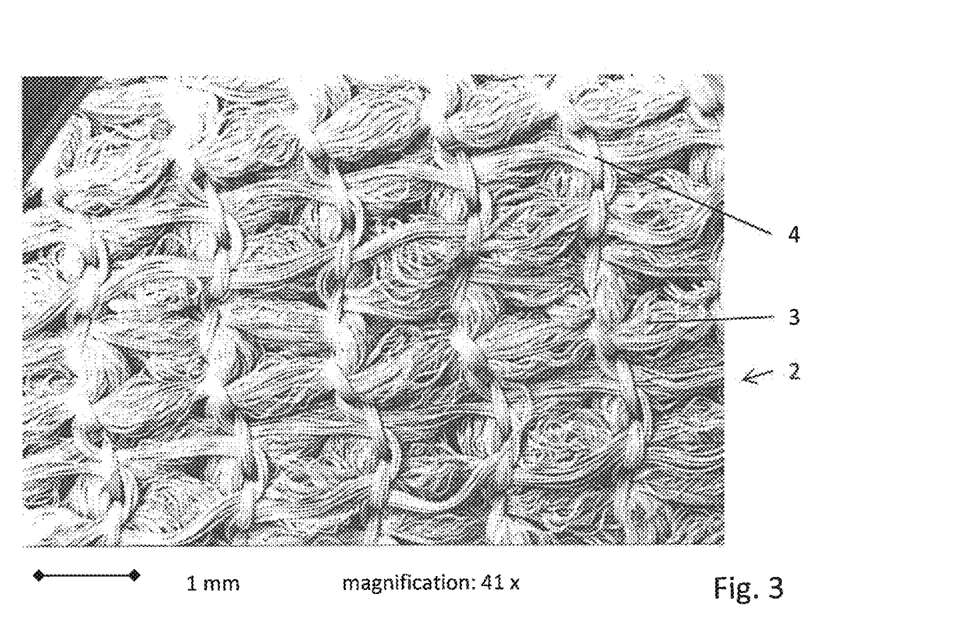
FIG. 3 shows a picture of the second surface of an inventive fabric with a magnification factor 41 times the actual size after the microfibers are subjected to splitting, mechanically roughened and cut, but before loading the microfibers are with any active agents.
Figure 4:
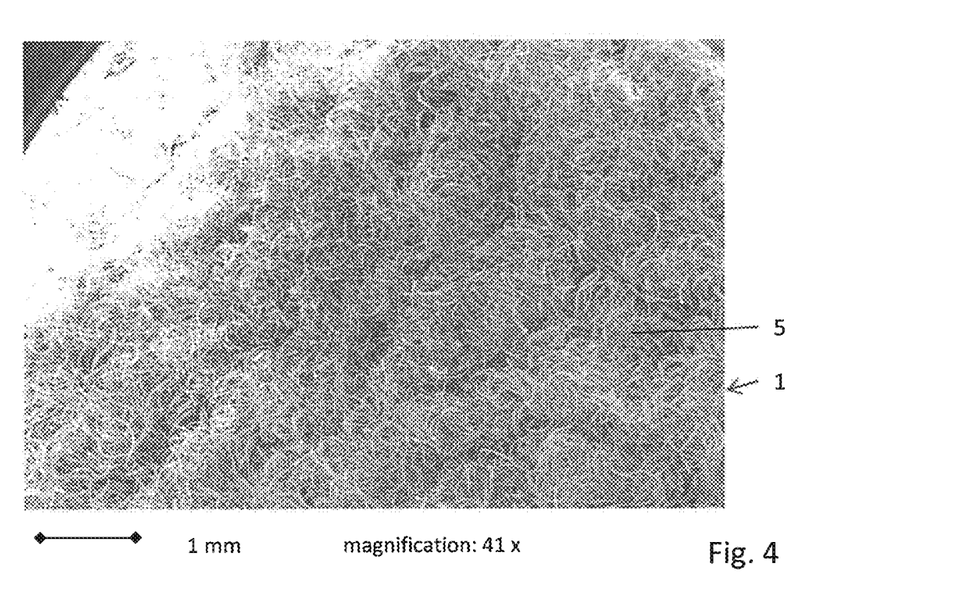
FIG. 4 shows a picture of the first surface of an inventive fabric with a magnification factor 41 times the actual size after the microfibers are subjected to splitting, mechanically roughened and cut, but before loading the microfibers with any active agents.

FIGS. 3 and 4 show the same fabric as FIGS. 1 and 2, except that the fabric shown in FIGS. 3 and 4 has further been subjected to a splitting process by an alkaline solution treatment. The alkaline solution treatment splits each microfiber 3 (FIG. 3) so as to produce fine fibers or filaments 5, which also are shown in FIG. 4. Each of edge views of FIGS. 7 and 8 respectively provides a magnified view of the microfibers 3 before undergoing the splitting process (FIG. 7) and after they have been split (FIG. 8) to become the filaments 5. After each microfiber 3 shown in FIG. 3 undergoes the alkaline solution treatment, the resulting fine fibers or filaments 5 (FIG. 4) become closely packed in a parallel structure forming interstices having a capillary effect in the first surface 1 shown in FIG. 4, thereby increasing the liquid absorbency of the first surface 1. The water absorbency of this resulting fabric shown in FIGS. 4-10 is least four times its surface weight.

The first surface 1 shown in FIG. 4 also has been mechanically roughened and cut, thereby rendering the first surface 1 fluffy and yet short-haired and compact in order to result in a further surface enlargement of the fabric structure. Thus, the filaments 5 shown in FIG. 4 produce an abrasive effect when contacting the skin of the user of the inventive fabric. Desirably, mechanically roughening the first surface 1 can be achieved by sticking and plucking the first surface 1 with a retroserrate comb, which has tooth-like projections pointing away from the apex of the comb. During mechanical roughening, small fibers are plucked out of the fabric. After completing the mechanical roughening, the mechanically roughened first surface 1 is cut by being mowed by a machine that razor cuts the first surface 1 to a predefined length, which can be selected to suit the intended application of the fabric. Moreover, the mechanically roughened and cut first surface 1 reduces the ability of the fabric to shed loose fibers from the fabric, and accordingly minimizes the fibers available to adhere to the user's skin during and immediately after use of the fabric.

Figure 5:
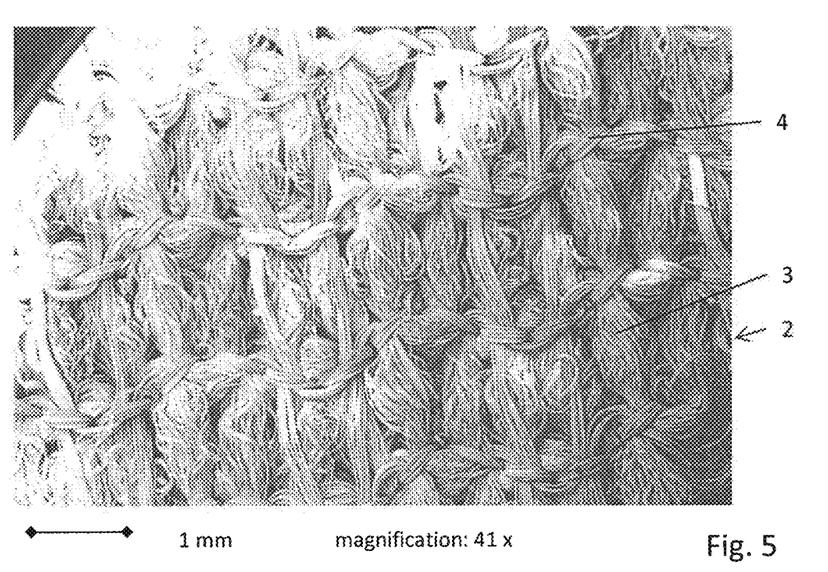
FIG. 5 shows a picture of the second surface of a finished inventive fabric, with a magnification factor 41 times the actual size.
Figure 6:
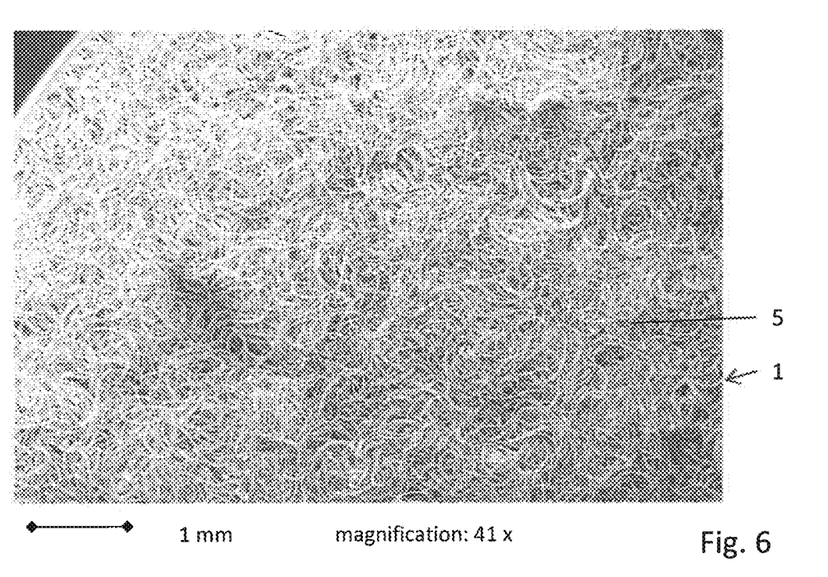
FIG. 6 shows a picture of the first surface of a finished inventive fabric, with a magnification factor 41 times the actual size.

FIGS. 5 and 6 show the same fabric as FIGS. 3 and 4, except that the fabric shown in FIGS. 5 and 6 has further been loaded with medical, pharmaceutical or cosmetic active agents, which cannot be discerned by the naked eye in FIGS. 5 and 6. Preferably, the second surface 2 shown in FIG. 5 is not roughened and thus firm and readily able to be gripped by the user. Furthermore, according to a presently preferred embodiment, the fabric shown in FIGS. 5 and 6 has further been compressed and/or sanforized to become more compact, and such treatment further minimizes the fibers available to adhere to the user's skin during and immediately after use of the fabric.

As an example, the microfibers may comprise 40% by weight of polyamide and 60% by weight of polyester, +1-5% in each case. Additionally, the microfibers desirably may weigh in the range of about 150-200 dtex.

According to the pictures shown in all figures of the skin care fabric, the fabric comprises in addition to the microfiber 3, a pure polyamide fiber 4 which may have a weight in the range of about of 38-55 dtex. The splitting process resulting from an alkaline solution treatment does not split the pure polyamide fiber 4, which easily can be identified in the figures.

It has been found that a presently preferred fabric according to the invention has an average pile height on the fluffy, first surface 1 in a range of about 10% to 60% of the total thickness of the fabric, preferably in a range of about 25-55%. Also, the warp-knitted fabric desirably has a stitch count in a range of about 16-20 stitches per centimeter.

In some embodiments, the active agents desirably are encapsulated in liposomes. Preferably, the active agents are particles having diameters in the range of between about 20 and 130 nanometers.

The fabric may be loaded with active agents in the range of between about 5 g to 20 g of the active agents per square meter of the fabric, preferably in the range of between about 9 g to 15 g/m$^2$. Embodiments of individual sheets of the fabric desirably may have an area of between about 100-300 cm$^2$, preferably about 190-220 cm$^2$.

Figure 7:
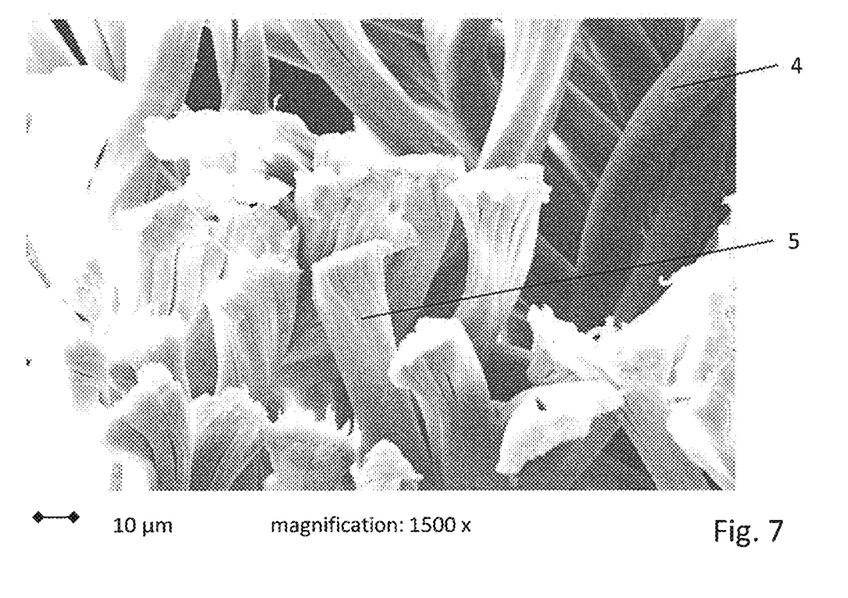
FIG. 7 shows a picture of the cut side of the fibers of an inventive fabric with a magnification factor 1500 times the actual size but before the microfibers are subjected to splitting.
Figure 8:
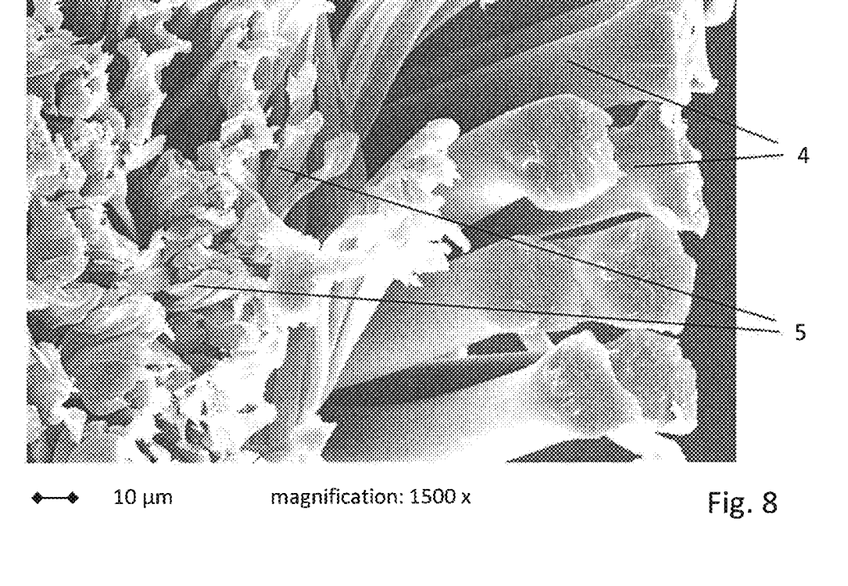
FIG. 8 shows a picture of the cut side of the fibers of a finished inventive fabric, with a magnification factor 1500 times the actual size.

FIGS. 7 and 8 show the fibers present in the fabric according to the FIGS. 1 and 2 (FIG. 7) and the FIGS. 5 and 6 (FIG. 8), but in an enlarged view. In comparing the state of the fabric at the different stages shown in these figures, it can be seen that the microfibers 3 build a string before splitting and are separated in single filament fibers 5 after splitting. Furthermore, it can be seen that each of the polyamide fibers 4 does not split when subjected to the alkaline solution treatment, but rather remains intact and solid.

Figure 9:
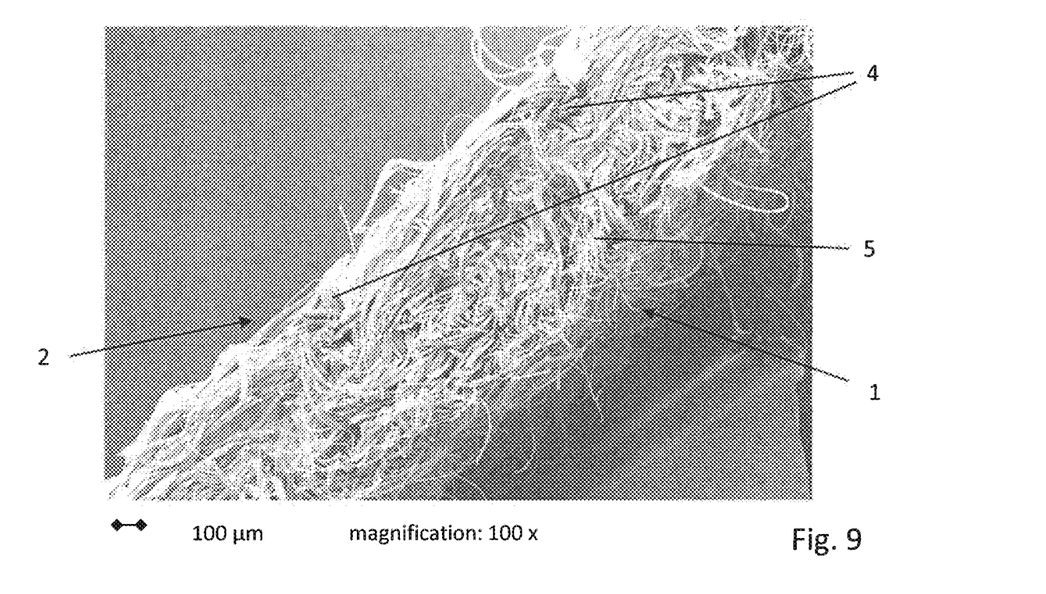
FIG. 9 shows a picture of an end edge view of a finished fabric according to the invention, with a magnification factor 100 times the actual size.
Figure 10:
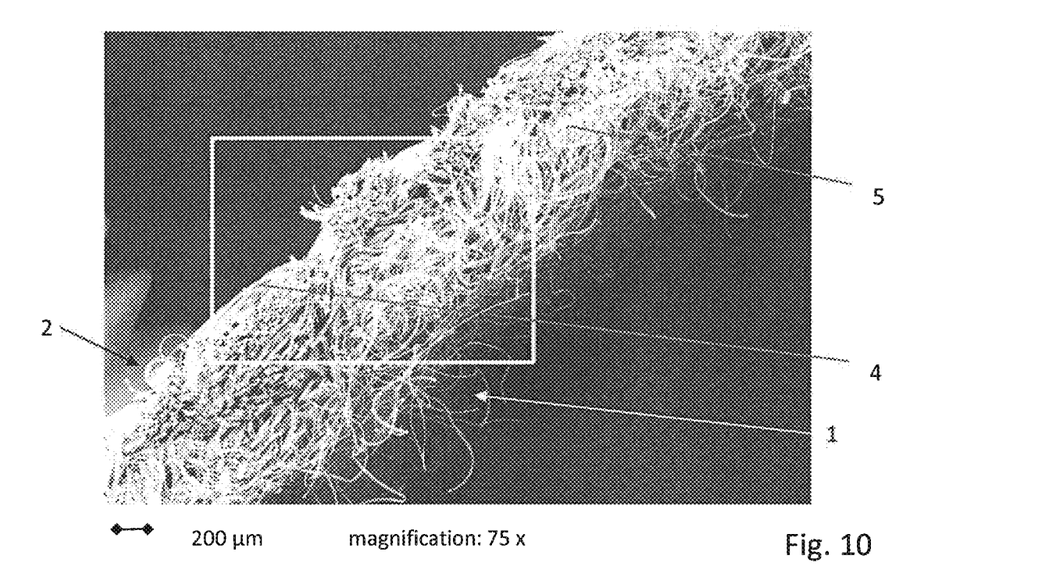
FIG. 10 shows a picture of an end edge view of a finished fabric according to the invention, with a magnification factor 75 times the actual size.

FIGS. 9-12 show end edge views (revealed by a transverse cut through a sheet) of the finished fabric according to the invention with different degrees of enlargement. In FIGS. 9 and 10, the polyamide fiber 4, which holds together the fabric even after the mechanical treatment, is near to the second surface 2, while the first surface 1 is fluffy with the filaments 5.

Figure 11:
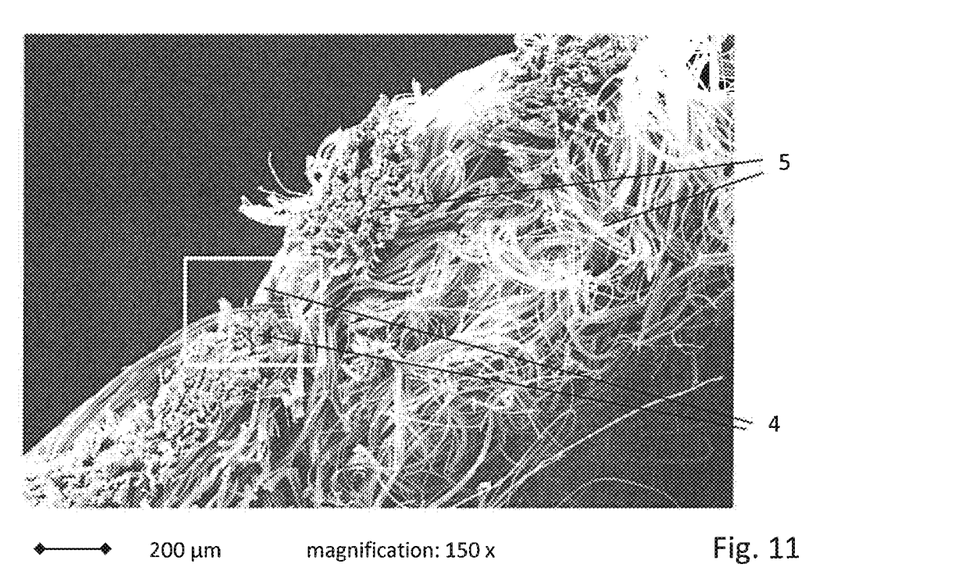
FIG. 11 shows an enlarged view of the section outlined by the square in the picture of FIG. 10, with a magnification factor 150 times the actual size shown in FIG. 10.
Figure 12:
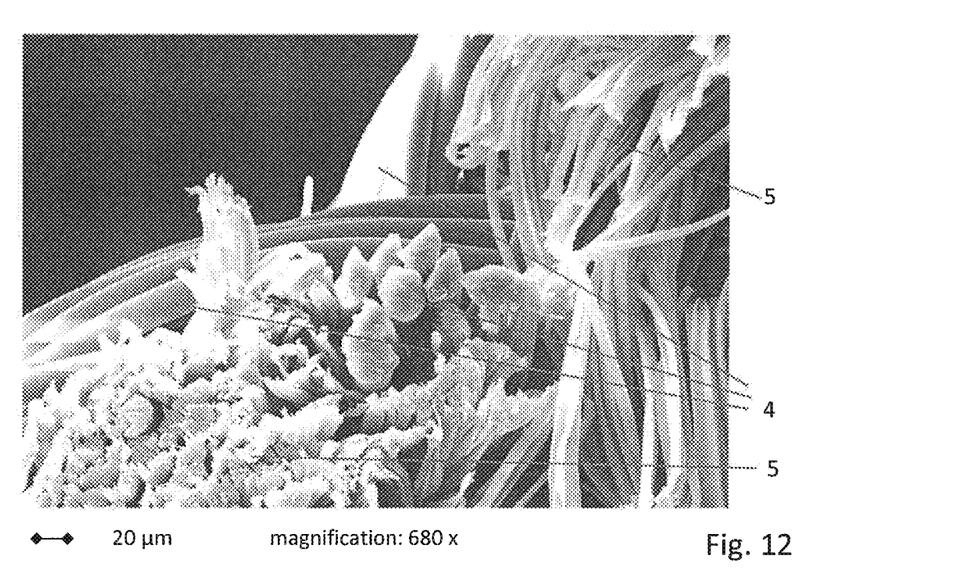
FIG. 12 shows an enlarged view of the section outlined by the square in the picture of FIG. 11, with a magnification factor 680 times the actual size shown in FIG. 11.

As indicated by the rectangle shown in FIGS. 10 and 11, each of FIGS. 11 and 12 shows a further enlargement of a section taken from its respective previous FIGS. 10 and 11. The polyamide fibers 4 easily can be identified and distinguished from the filament fibers 5 of the microfibers 3 that have been split due to having undergone the alkaline solution treatment.

Embodiments of the fabric according to the invention showed good results in water absorption tests and are preferred in skin use of all kinds, including facial uses, medical uses, pharmaceutical uses and cosmetic uses.

LIST OF REFERENCE NUMERALS

1 First surface
2 Second surface
3 Microfiber
4 Polyamid fiber
5 Filament of the micro fiber after splitting

What is claimed is:

1. A skin care fabric for medical, pharmaceutical or cosmetic use comprising:
   a warp-knitted fabric having a surface weight of less than 180 g/m2 and at least 80% by weight of microfibers whose fibers have a diameter of less than 50 microns and are a mixture of polyamide and polyester, the warp-knitted fabric defining a first surface and a second surface disposed opposite the first surface; and
   active agents carried by the warp-knitted fabric and promoting an effect that is medical, pharmaceutical or cosmetic;
   wherein the microfibers are split and closely packed in a parallel structure having a capillary effect and an abrasive effect;
   wherein the first surface is mechanically roughened and cut making it fluffy and yet short-haired and compact in order to leave as few fibers as possible on the skin during use and resulting in a further surface enlargement of the unroughened first surface; and wherein the warp-knitted fabric has a water absorbency of at least four times the surface weight of the warp-knitted fabric.

2. The skin care fabric according to claim 1, wherein the second surface is not roughened and thus grippy and firm.

3. The skin care fabric according to claim 1, wherein the fabric has been sanforized to become more compact.

4. The skin care fabric according to claim 1, wherein the microfibers comprise 40% by weight of polyamide and 60% by weight of polyester, +1-5% in each case.

5. The skin care fabric according to claim 1, wherein the microfibers weigh 150-200 dtex.

6. The skin care fabric according to claim 1, wherein in addition to the microfiber, the fabric comprises a pure polyamide fiber with a weight of 38-55 dtex.

7. The skin care fabric according to claim 1, wherein the pile height averages 10% to 60% of the total thickness of the fabric.

8. The skin care fabric according to claim 1, wherein the pile height averages 25 to 55% of the total thickness of the fabric.

9. The skin care fabric according to claim 1, wherein the warp-knitted fabric has a stitch count of 16-20 stitches per centimeter.

10. The skin care fabric according to claim 1, wherein the active agents are encapsulated in liposomes.

11. The skin care fabric according to claim 1, wherein the active agents are particles having diameters of between 20 and 130 nanometers.

12. The skin care fabric according to claim 1, wherein the fabric is loaded with 5 g to 20 g of active agents per square meter of the fabric.

13. The skin care fabric according to claim 1, wherein the fabric is loaded with 9 g to 15 g of active agents per square meter of the fabric.

14. The skin care fabric according to claim 1, wherein the fabric has an area of about 100-300 cm2.

15. The skin care fabric according to claim 1, wherein the fabric has an area of about 190-220 cm2.

16. A method of producing a skin care fabric for medical, pharmaceutical or cosmetic use, the method comprising the steps of:
providing a warp-knitted fabric having a surface weight of less than 180 g/m2 and at least 80% by weight of microfibers having a diameter of less than 50 microns, wherein the microfibers include polyamide fibers and polyester fibers, the warp-knitted fabric defining a first surface and a second surface disposed opposite the first surface;
subjecting the warp-knitted fabric to an alkaline solution treatment that splits the microfibers into fine fibers;
mechanically roughening the first surface until it becomes fluffy;
mowing the first surface with a razor cut;
compressing the first surface so as to closely pack the fine fibers in a parallel structure having a capillary effect and an abrasive effect; and
loading the warp-knitted fabric with medical, pharmaceutical or cosmetic active agents.

17. The method according to claim 16, wherein a retroserrate comb is used for mechanically roughening the first surface.

18. The method according to claim 16, wherein compressing the first surface is effected during sanforizing the warp-knitted fabric.

* * * * *